United States Patent [19]

Lindwer

[11] Patent Number: 5,032,134
[45] Date of Patent: Jul. 16, 1991

[54] JOINT PROSTHESIS AND TOOL TO BE USED THEREWITH

[76] Inventor: Jonas Lindwer, Stokhorstlaan 98, 7531 JH Enschede, Netherlands

[21] Appl. No.: 351,251

[22] Filed: Apr. 21, 1989

Related U.S. Application Data

[63] Continuation of Ser. No. 681,327, Dec. 13, 1984, abandoned.

[30] Foreign Application Priority Data

Dec. 16, 1983 [NL] Netherlands .......................... 8304339

[51] Int. Cl.⁵ ................................................ A61F 2/32
[52] U.S. Cl. ........................................ 623/23; 623/22; 623/20
[58] Field of Search ...................................... 623/16–23

[56] References Cited

U.S. PATENT DOCUMENTS

| | | | |
|---|---|---|---|
| 4,259,072 | 3/1981 | Hirabayashi et al. | 3/1.913 |
| 4,280,233 | 7/1981 | Raab | 3/1.913 |
| 4,283,799 | 8/1981 | Pratt et al. | 3/1.913 |
| 4,290,338 | 9/1981 | Gruber | 411/21 |
| 4,454,612 | 6/1984 | McDaniel et al. | 3/1.913 |

FOREIGN PATENT DOCUMENTS

| | | | |
|---|---|---|---|
| 2305442 | 8/1974 | Fed. Rep. of Germany | 128/92 C |
| 2733826 | 2/1979 | Fed. Rep. of Germany | 623/23 |
| 2519248 | 7/1983 | France | 3/1.912 |
| 457981 | 8/1968 | Switzerland | 411/21 |

Primary Examiner—David J. Isabella
Attorney, Agent, or Firm—Watson, Cole, Grindle & Watson

[57] ABSTRACT

A joint prosthesis comprising two co-operating prosthesis members fastening each to a different joint bone. At least one of the prosthesis members is formed by at least two prosthesis elements one surrounding the other, the one prosthesis element adjacent the bone being provided with fastening means distributed along the outer face and being located inside the outer face when the joint prosthesis is being applied, out of which outer face they can subsequently be moved in order to cause them to penetrate into the bone.

The fastening means are formed by pins guided in passages of the prosthesis element. The tipform of these pins could be chosen in relation to the hardness of the bone to be penetrated.

Furthermore, the contact faces of the two prosthesis elements could be provided with coating mimicing the elastic and/or resilient features of bone.

11 Claims, 3 Drawing Sheets

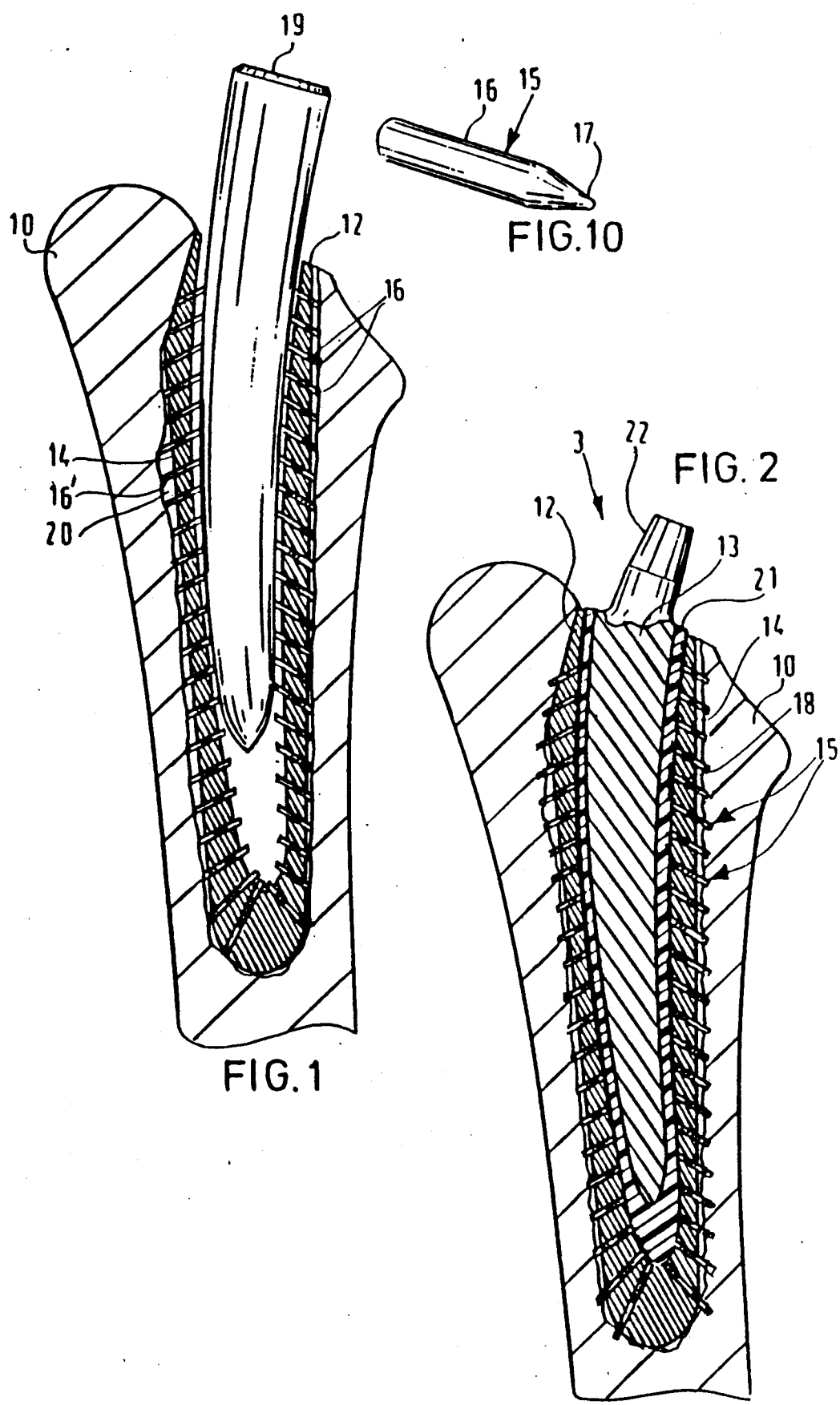

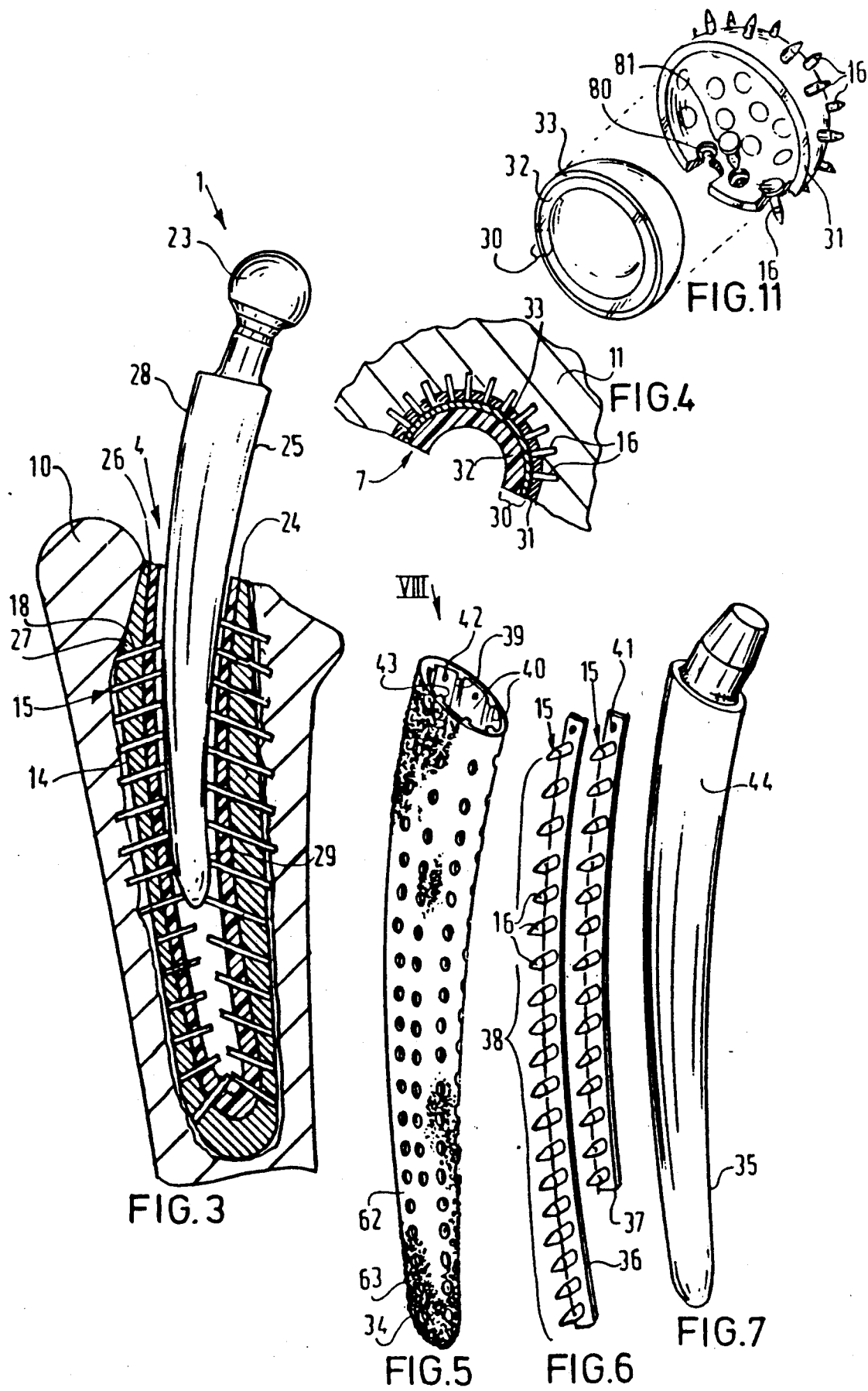

JOINT PROSTHESIS AND TOOL TO BE USED THEREWITH

This application in a continuation of application Ser. No. 681,327, filed 12/13/84 now abandoned.

The invention relates to a joint prosthesis comprising two co-operating prosthesis members each fastened to a different joint bone.

Such a joint prosthesis is known. At present at least two different methods and known to fasten the prosthesis members to a joint bone. A first method consists of applying a layer of cement between a prosthesis member and a joint bone which layer firmly fixes this prosthesis member to the joint bone after curing. The use of cement is attended with various disadvantages. In the first place the cement becomes brittle in the course of time, it scales off and due to these aging phenomena the prosthesis member becomes loose from the joint bone. In the second place the cement affects the adjacent bone layer. Finally a patient may be allergic to constituents of the cement.

In another method of fastening a prosthesis member to a joint bone, cement is not used. Instead, this method uses a prosthesis member having a coating applied thereto which stimulates bone growth thereon so that after some time the joint bone grows in a natural manner and thus attaches the prosthesis member to it. A disadvantage of this method is that if movement occurs between the bone and the prosthesis device during development of the attachment, the natural growth must begin anew. In practice, this means that the patient must refrain from overloading the joint during the growth and attachment process, giving rise to various physical problems for the patient.

The invention has for its object to improve the joint prosthesis of the kind set forth in the preamble in a sense such that, though the use of cement after the application of a prosthesis member is dispensed with, the prosthesis member is directly firmly fixed inside the joint bone. According to the invention this is achieved in that at least one of the prosthesis members is composed of at least two prosthesis elements surrounding one another, whilst one prosthesis element adjacent the bone is provided with fastening means distributed along its outer face adjacent the bone and being located inside the outer face when the prosthesis is applied, which members can subsequently be displaced out of this outer face in order to cause them to penetrate into the bone.

This primary fixation of the prosthesis members to the joint bone is particularly reliable because along the whole outer face of one prosthesis element the fastening means penetrate into the bone and since a large number of fastening means are used, the depth of penetration of the fastening means into the bone can be limited, for example, to an order of magnitude of 1 to 4 mms. In this way the disadvantages of the use of long screws are also avoided.

In a very simple manner a large number of pins can be simultaneously arranged inside the prosthesis member, when sequences of pins are fastened to a strip material, whilst a prosthesis element is preferably provided with a slot for receiving the strip of material.

When a strip of material is fastened at one end to the prosthesis element, it is possible, in a later stage, for example for applying a new prosthesis member, to simultaneously remove large series of pins from the prosthesis member.

Since the bone has a definite elasticity and resilience and the prosthesis members, and certainly those used as a hip prosthesis, are mainly made of metal, it is preferred to impart to these prosthesis members the elasticity and resilience approaching those of the bone. This can be achieved in that at least one of the relative contact faces of the two prosthesis elements is provided with a coating of a resilient synthetic resin, preferably polyethylene.

When a coating of resilient synthetic resin is used the fastening means can be advantageously arranged in the prosthesis member, when the synthetic resin coating is fastened to one prosthesis element and forms a force fit to the fastening means at the level of the passages provided therein.

In order to obtain a wide range of exchangeability it is preferred to provide the same shapes and sizes of the contact faces for relatively different types for the one and the other prosthesis element.

In order to prevent the prosthesis elements surrounding one another from performing a relative displacement it is preferred to releasably guard the one and the other prosthesis element with the aid of guard means.

A particularly advantageous embodiment of the invention is characterized in that the joint prosthesis is a hip prosthesis in which the prosthesis member to be arranged in the bone is formed by the one prosthesis element in the form of an envelope having a passage, the internal shape of the envelope substantially corresponding with the external shape of the part of the other prosthesis element to be inserted into it in the form of a stem, the other part of which designed as a head and fastened to said stem corresponding with the second prosthesis member to be arranged in the pelvis in the form of a socket.

A further aspect of the invention relates to a tool for driving outwards the fastening means of the one prosthesis element after the application of the latter.

The above mentioned and further features will become apparent from five embodiments given by way of non-limitative examples of the hip prosthesis in accordance with the invention with reference to the accompanying drawing.

The drawings show in

FIG. 1 and FIG. 2 an elevational view and partly a sectional view of a prosthesis member to be arranged and arranged respectively in accordance with the invention;

FIG. 3 an elevational view like FIG. 1 of a second embodiment of a prosthesis member in accordance with the invention.;

FIGS. 4 and 11 each an elevational view of the prosthesis member of FIG. 3 co-operating with a second member fastened in another joint bone;

FIGS. 5, 6 and 7 the component parts of a third embodiment of a prosthesis member in accordance with the invention;

FIG. 8 an enlarged scale, a variant of detail VIII of FIG. 6 of a fourth embodiment of a prosthesis member in accordance with the invention;

FIG. 9 a knee joint comprising a joint prosthesis having two co-operating prosthesis members in a fifth embodiment of the invention; and FIG. 10 an enlarged scale, a fastening means in accordance with the invention.

DETAILED DESCRIPTION OF PREFERRED EMBODIMENTS

Figure 8:
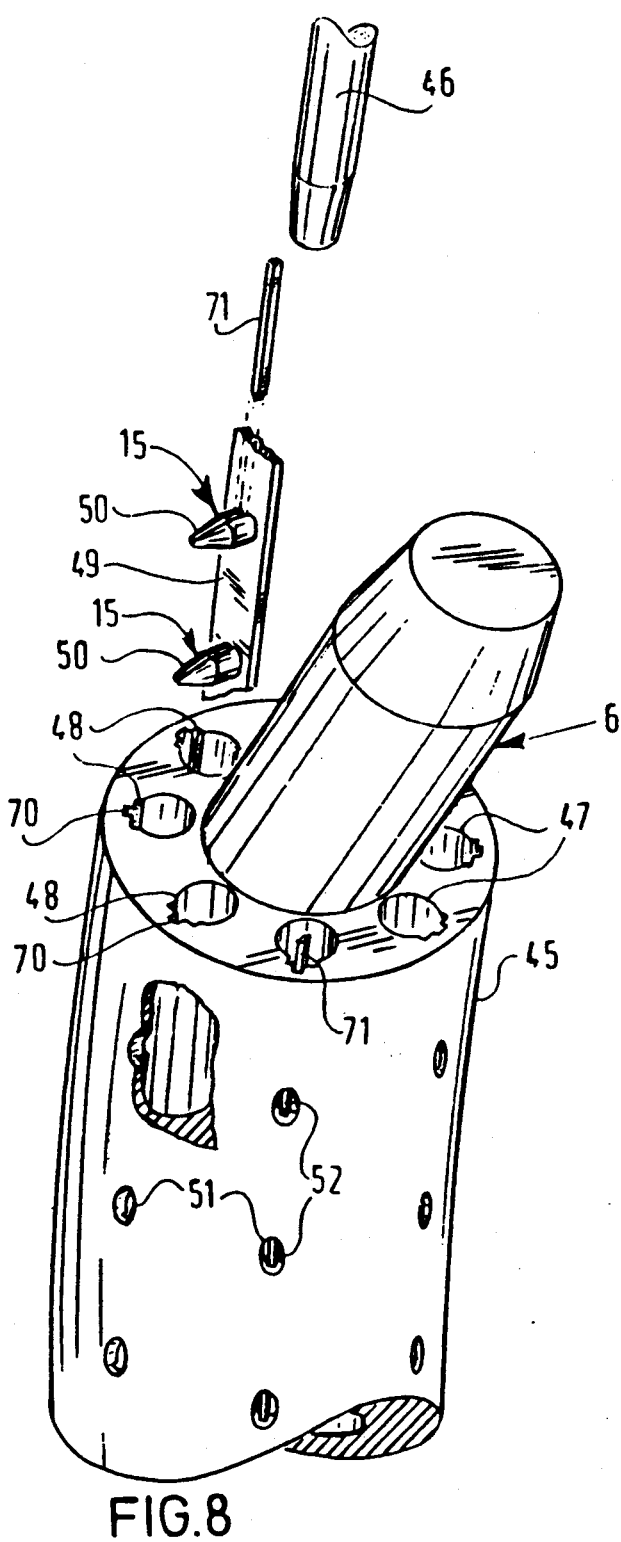

FIGS. 1 and 2 illustrate the sequence of applying a joint prosthesis 3 to a bone 10. The prosthesis comprises two cooperating members 12 and 13, the former of which is illustrated as being fixed in place in FIG. 1 whereas the two members in cooperating relation are illustrated in FIG. 2. In FIG. 1, the member 12 has been inserted into a recess or passage in the bone 10 and as illustrated, is in the form of a member whose wall presents an outer surface 14 which is disposed in opposed relation to the passage or recess surface of the bone 10 and whose inner surface is of generally tapered form. The wall is provided with a plurality of openings or passages 18 which slidably receive a plurality of pin or fastening means 15. Each of these pin means is of elongate form so as to present a body 16 and a tip end which is of conical, rounded off form such as is illustrated at 17 in FIG. 10. Since the pin means are slidable in the openings 18 in the wall of the member 12, they are retracted when the member is inserted in place so that their tips clear the bone tissue whereas their inner ends are projected within the hollow interior of the member 12. When the member is in place, the punch or similar tool 19 is driven into the interior of the member 12 as is illustrated in FIG. 1 to force the pin means 15 outwardly so that their tips 17 penetrate into the bone and thus anchor the member 12 in place.

Since the bone 10 may have parts of differing hardness, the form of the tips 17 of the pins may be chosen optimally with respect to these different parts of the bone. Thus, the tips may be provided with an acute tip for hard bone areas and with blunt tips for softer bone areas in order to obtain an optimum fixation of all of the pins. Prior to implanting the pins as illustrated in FIG. 1, the hardness of the various bone parts may be determined by means of tools known in the art. When the element 12 is inserted, the tips of the pins are located or retracted inside the outer face or surface 14 of the wall of the prosthesis member 12. Then, when the pins are forced outwardly by means of the tool 19, the pins are guided in their respective passages 18 to penetrate the bone. Because the pins are distributed generally throughout the surface 14, it is not necessary for all of the pins to penetrate into the bone 10. For example, at such places as at the cavity 20 as illustrated, a pin 16' projecting at that location or region may extend only up to or into contact with the bone.

After the pins have been forced outwardly by means of the tool 19, and after removing the tool, the inner prosthesis element 13 may be inserted in place in substantially fully seated relation with the inner surface of the outer prosthesis device 12, as is illustrated in FIG. 2. The prosthesis element 13 is provided with an external layer 21 of resilient synthetic resin such as polyethylene so that a resilient layer or cushion is provided whose elastic and resilient properties correspond with those of the bone 10. After the insertion of the element 13, a spherical ball may be provided on the stub 22 which, in cooperation with a suitable socket, provides an artificial joint means in association with prosthesis means provided on the other bone of the bone joint. Alternatively, such spherical ball may be formed integrally with the exposed or exterior end of the prosthesis device as, for example, is illustrated in FIG. 3 at 23.

Thus the prosthesis member 3 consists of a prosthesis element 12 mainly having the form of a sleeve and a stemshaped prosthesis element 13 arranged in said sleeve. The prosthesis elements 12 and 13 together mainly correspond with a stem of a known stem-shaped prosthesis member, the difference being that in accordance with the invention the prosthesis member is provided with outwardly displaceable fastening means.

FIGS. 3 and 4 show a second embodiment of prosthesis members 4 and 7 associated with the joint prosthesis 1, a hip prosthesis.

The prosthesis member 4 has substantially the same construction as the prosthesis member 3 (FIGS. 1 and 2), the difference being that the synthetic resin coating 24 between the relative contact faces 25 and 26 forms part of the sleeve-shaped prosthesis element 27, in which the stem-shaped prosthesis element 28 is arranged. This construction has the advantage that the one prosthesis element 27 provided with the internal synthetic resin coating 24 establishes, at the passages 18 provided therein, a force fit with the fastening means 16 so that during the application of the prosthesis element 27 in the bone 10 said means are retained therein without being able to become free from the passages 18 or to protrude from the outer face 14. Since the prosthesis element 28 has a smooth metal surface 25, the use of a punch 19 can be dispensed with when the fastening means 16 are being expelled. Moreover, by their ends 29, the fastening means 16 exert pressure on the metal surface 25 so that between the fastening means 16 and the prosthesis element 28 no or hardly any resilience and hence no relative displacement are possible as compared to the situation illustrated in FIGS. 1 and 2.

FIG. 4 shows the prosthesis member 7 which can co-operate with the prosthesis member 4 of FIG. 3, and arranged in the joint bone 11, in this case the pelvis. The prosthesis member 7 comprises the prosthesis elements 30 and surrounding one another. The prosthesis element 30 co-operating with the spherical ball 23 consists of a synthetic resin layer 32 surrounded by a metal coating 33. In this way the pins 16 are prevented from penetrating into the synthetic resin layer 32. From the exploded view of FIG. 11 it will be apparent that the fastening means 16 are expelled with the aid of the prosthesis element 30, whilst a rim 81 of the fastening means is received in a rod 80.

FIGS. 5, 6 and 7 show a third embodiment of a prosthesis member in accordance with the invention which comprises a sleeve-shaped prosthesis element 34 surrounding stem-shaped prosthesis element 35.

In this case the fastening means 16 are arranged on a strip of material 36, 37 of different lengths dependent on the shape of the prosthesis element 34. Also in this case strips of material could be used, having pins with a tipform adapted to the hardness or the bone to be penetrated. If the strips are to be provided with pins having different tip-forms, then it is advantageous that these pins are mounted releasably on the strip. Thus the sequences of pins 16 can be accommadated in the prosthesis element 34, which for this purpose has in its internal face 39 slots 40 for receiving the strips of material 36 and 37 respectively. The strips of material 36, 37 can be fixed with the aid of appropriate fastening means 41, 42 in the prosthesis element 34. Since the strips of material 36, 37 are located in the slots 40, a smooth internal surface 43 is formed inside the prosthesis element 34, said surface having a shape matching the external face 44 of the prosthesis element 35.

FIG. 8 shows a detail of a prosthesis member 6 in a fourth embodiment of the invention comprising a prosthesis element 45 having a plurality of bores 47 adapted to receive prosthesis elements 46. Also in this case the prosthesis elements 46 are surrounded by the prosthesis element 45. The bores 47 also have slots 48 for receiving strips of material 49 provided in this case with sequences of fastening means 15 in the form of split pins 50. In order to ensure splitting of the split pins 50 when they are expelled by the action of the prosthesis element 46, splitting partitions 52 are provided in passages 51. These splitting partitions form part of a metal strip 71 to be arranged in a groove 70. The passages 51 may also be formed by gaps extending in the direction of length of the prosthesis element 45. This has the advantage that several series of fastening means can be moved to the ouside through a gap. Moreover, the tolerance in the direction of length of a gap is less critical with respect to the fastening means to be passed through.

Figure 9:
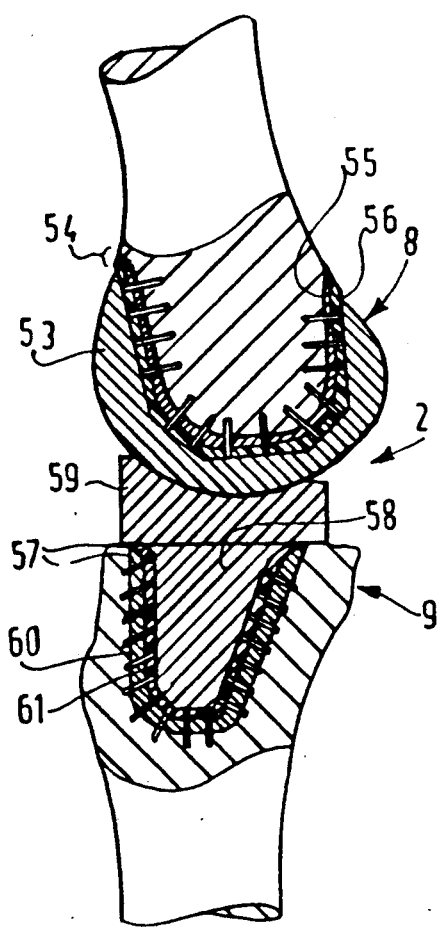

A fifth embodiment of prosthesis members 8, 9 of, in this case, a knee prosthesis 2 in accordance with the invention is shown in FIG. 9. The prosthesis member 8 comprises a prosthesis element 53 surrounding a prosthesis element 54. The prosthesis element 54 consists of a metal layer 55 and a synthetic resin coating 56.

The prosthesis element 9 comprises a prosthesis element 57 surrounding a synthetic resin prosthesis element 58, the part 59 of which co-operates with the prosthesis element 53. The prosthesis element 57 comprises a metal layer 60 and an inner synthetic resin coating 61 applied thereto. Since the prosthesis element 58 is made from a synthetic resin, the coating 61 may, if desired, be dispensed with.

It will be obvious that for the various metal parts of the joint prosthesis 1 and 2 metals are chosen which do not react or react only to a negligible extent with respect to neighoring bone or soft tissue. Those materials are known in the art and are stainless steel, titanium, and cobalt chromium alloys. As is shown by way of example in FIG. 5, the external surface of the prosthesis element adjacent the bone, for example in this case the prosthesis element 34 may be provided on the surface 62 with pellets 63 of, for example, cobalt chromium molybdenum alloys such as Francobal having a secondary/bone growth stimylating stimulating effect so that not only by the primary fixation with the aid of the fastening means 15 but also secondary bone growth additionally fixes the prosthesis element 34 inside the bone by natural agency.

I claim:

1. A prosthesis for providing a hip joint between the thigh and pelvis bones without the use of cementitious material to effect anchoring of the prosthesis to bone, comprising the combination of:
   a first outer prosthesis member defining a wall having an outer surface for interfitted reception within a recess extending into an end of the thigh bone, and a tapered inner surface, said first outer prosthesis member having a plurality of openings through said wall;
   a first inner prosthesis member having a solid body presenting a tapered out surface formed in generally complimentary fashion with respect to said inner surface of said wall, said body being received within said first outer prosthesis member and there being first joint means at that end of the body external to said first outer prosthesis member for transmitting forces imposed thereon directly to said first outer prosthesis member through the intermediary of said body and said tapered surfaces;
   elongate first fastening means slidably received in said openings in said wall for movement between retracted positions in which outer ends of said first fastening means are withdrawn with respect to said outer surface of the wall, so as not to interfere with said interfitted reception while inner ends of the fastening means extend inwardly from said inner surface of the first wall, and extended positions in which the outer ends of the first fastening means project outwardly from the outer surface of the wall and penetrate into the thigh bone within whose recess the hollow first outer prosthesis member is interfitted while the inner ends of the first fastening means are moved toward said inner surface of the wall;
   a layer of resilient material between said outer surface of the first inner prosthesis member and the inner surface of the wall of the first outer prosthesis member, the outer surface of said first inner prosthesis member sandwiching said layer against the inner surface of the wall while constraining said outer ends of the fastening means to be retained in said extended positions thereof;
   a second inner prosthesis member which is of hollow form defining a second wall having an inner surface for interfitted reception of an end of the pelvis bone, said second inner prosthesis means having a plurality of openings through said second wall and said second wall defining an outer wall surface;
   a second outer prosthesis member having an inner surface formed in generally complimentary fashion with respect to said outer surface of said second wall;
   second elongate fastening means slidably received in said openings in said second wall for movement between retracted positions in which inner ends of said second fastening means are withdrawn with respect to said inner surface of the second wall while outer ends of the second fastening means extend outwardly from said outer surface of the second wall, and extended positions in which the inner ends of the second fastening means project inwardly from the inner surface of the second wall and penetrate into the end of the pelvis bone which is interfitted within said hollow second inner prosthesis means;
   a second layer of resilient material between said inner surface of the second outer prosthesis member and the outer surface of the second inner prosthesis member, the inner surface of said second inner prosthesis member sandwiching said second layer against the outer surface of the second wall while constraining said inner ends of the second fastening means to be retained in said extended positions thereof; and
   second joint means seated within said first joint means for providing a prosthetic hip joint between an exterior end of the second inner prosthesis member and an exterior end of the first inner prosthesis member.

2. A a prosthesis as defined in claim 1 including a second inner prosthesis means which is of hollow form defining a second wall having an inner surface for interfitted reception of an end of the pelvis bone, said second inner prosthesis means having a plurality of openings through said second wall and said second wall defining an outer wall surface;

second outer prosthesis means having an inner surface formed in generally complementary fashion with respect to said outer surface of said second wall;

second elongate fastening means slidably received in said openings in said second wall for movement between retracted positions in which inner ends of said second fastening means are withdrawn with respect to said inner surface of the second wall while outer ends of the second fastening means extend outwardly from said outer surface of the second wall, and extended positions in which the inner ends of the second fastening means project inwardly from the inner surface of the second wall and penetrate into the end of the pelvis bone which is interfitted within said second hollow inner prosthesis means;

a second layer of resilient material between said inner surface of the second outer prosthesis means and the outer surface of the second wall of the second inner prosthesis means, the inner surface of said second inner prosthesis means sandwiching said layer against the outer surface of the second wall while constraining said inner ends of the second fastening means to be retained in said extended positions thereof; and joint means for providing a prosthetic hip joint between an exterior end of the inner prosthesis means first mentioned and an exterior end of the second inner prosthesis means.

3. A a prosthesis as defined in claim 2 wherein said outer prosthesis means first mentioned is provided with at least one groove in its tapered surface, and including a strip received in said groove and carrying some of said fastening means.

4. A a prosthesis as defined in claim 1 wherein said outer prosthesis means is provided with at least one groove in its tapered surface, and including a strip received in said groove and carrying some of said fastening means.

5. A joint prosthesis comprising:
a first joint member having a ball at one end thereof and a second joint member having a socket configured to engage said ball to provide joint movement between a first and second bone;
first and second prosthesis means for receiving said first and second joint members respectively, said first and second prosthesis means disposed within said first and second bones respectively; and
first and second fastening means including a plurality of fastening elements configured for slidably passing through openings in said first and second prosthesis means and into penetration with adjacent bone thereby securing the first and second prosthesis means to the bone, at least one of said fastening means comprising a plurality of fastening pins and a carrying strip to which said fastening means are transversely secured.

6. A joint prosthesis as defined in claim 5 wherein the other prosthetic means of that pair thereof associated with said one of said fastening means is provided with a groove receiving said strip.

7. A prosthesis for providing one member of a prosthetic joint between two joint bones without the use of cementitious material to affect anchoring of the prosthesis to bone, said prosthesis comprising:
prosthesis means for penetration into and physical anchoring with a joint bone surface of one joint bone with which it is interfitted, said prosthesis means comprising first and second means having substantially complimentary surfaces for disposition in forcibly seated relation to each other, said first means defining a wall presenting said complimentary surface of the first means on one face thereof and another surface on the opposite face of the wall which is disposed in closely adjacent, interfitted relation to a surface of the one joint bone, joint means on said second means for receiving forces imposed thereon from said first means and the one joint bone through the intermediary of said complimentary surfaces and the forcibly seated relation thereof,
said first means having a plurality of openings therethrough and elongate fastening means slidable in said openings between a first position out of contact with said surface of the one joint bone but projected beyond the complimentary surface of said first means, thereby blocking said disposition of said complimentary surfaces in said forcibly seated relation to each other, and a bone penetrating second position when said complimentary surfaces are in said forcibly seated relation to each other, thereby anchoring said first means to the bone surface with which it is interfitted,
said first means provided with at least one groove in its complimentary surface and including a strip received in said groove configured for receiving said fastening means.

8. A prosthesis as defined in claim 7 including a layer of resilient material interposed between said complementary surfaces and maintaining them in substantially uniformly spaced relation.

9. A prosthesis as defined in claim 8 wherein said fastening means slidably penetrates said layer of resilient material.

10. A prosthesis for providing one member of a prosthetic joint between two joint bones without the use of cementitious material to effect anchoring of the prosthesis to bone, the prosthesis comprising:
prosthesis means for penetration into and physical anchoring with a joint bone surface of one joint bone with which it is interfitted, said prosthesis means comprising first and second means having substantially complimentary surfaces for disposition in forcibly seated relation to each other, said first means defining a wall presenting said complimentary surface of the first means on one face thereof and another surface on the opposite face of the wall which is disposed in closely adjacent, interfitted relation to a surface of the one joint bone, joint means on said second means for receiving forces imposed thereon from the other joint bone and for directly transmitting such forces to said first means and the one joint bone through the intermediary of said complimentary surfaces and the forcibly seated relation thereof,
said first means having a plurality of openings therethrough and elongate fastening means slidable in said openings between a first position out of contact with said surface of the one joint bone but projected beyond the complimentary surface of said first means thereby blocking said disposition of said complimentary surfaces and said forcibly seated relation to each other, and a bone-penetrating second position when said complimentary surfaces are in said forcibly seated relation to each other, thereby anchoring said first means to the bone surface with which it is interfitted, said prosthesis further comprising a layer of resilient material interposed between said complimentary surfaces and maintaining them in substantially uniformly space relation.

11. A prosthesis as defined in claim 10 wherein said fastening means slidably penetrates said layer of resilient material.

* * * * *